United States Patent [19]

Morinaka et al.

[11] Patent Number: 4,668,831

[45] Date of Patent: May 26, 1987

[54] TERT-BUTYL-HALOPHENOLS

[75] Inventors: Hideo Morinaka; Akira Nakanishi, both of Shin Nanyo; Yuji Nonaka, Tokuyama, all of Japan

[73] Assignee: Toyo Soda Manufacturing Co., Ltd., Nanyo, Japan

[21] Appl. No.: 840,488

[22] Filed: Mar. 14, 1986

Related U.S. Application Data

[62] Division of Ser. No. 771,798, Sep. 3, 1985, abandoned.

[30] Foreign Application Priority Data

Sep. 3, 1984 [JP] Japan ................................. 59-182695
Sep. 3, 1984 [JP] Japan ................................. 59-182696

[51] Int. Cl.$^4$ ............................................. C07C 39/28
[52] U.S. Cl. ..................................... 568/779; 568/774
[58] Field of Search ................................. 568/774, 779

[56]  References Cited

U.S. PATENT DOCUMENTS 2,318,390  5/1943  Hartmann et al. ................... 568/774
3,510,528  5/1970  Stevick et al. ....................... 568/774
3,920,757  11/1975 Watson ................................. 568/774
4,154,968  5/1979  Perrin et al. ......................... 568/774
4,277,629  7/1981  Binns .................................... 568/774

FOREIGN PATENT DOCUMENTS 80139    4/1975  Australia ............................. 568/779
247410   9/1911  Fed. Rep. of Germany ...... 568/779
58092    9/1911  Switzerland ........................ 568/779
9488601  2/1964  United Kingdom ................ 568/779

OTHER PUBLICATIONS

Zavgoyodgy, "J. General Chemistry, USSR" (1943), pp. 74–76.
Kaeding, "J. Organic Chemistry", vol. 26 (1961), pp. 4851–4855.

Primary Examiner—Werren B. Lone
Attorney, Agent, or Firm—Oblon, Fisher, Spivak, McClelland & Maier

[57]  ABSTRACT 3-tert-Butyl-4-halophenols which are useful as intermediates for preparing compounds having medical or agricultural activities.

3 Claims, No Drawings

TERT-BUTYL-HALOPHENOLS

This application is a division of application Ser. No. 771,798, filed Sept. 3, 1985, now abandoned.

FIELD OF THE INVENTION

This invention concerns 3-tert-butyl-4-halophenols which are novel compounds.

3-tert-Butyl-4-halophenols are useful as intermediates for providing substances capable of being employed as medicine or agricultural chemicals.

BACKGROUND OF THE INVENTION 3-tert-Butyl-4-halophenols of this invention are novel compounds which have never been described in any literature before.

DETAILED DESCRIPTION OF THE INVENTION

The object of this invention lies in providing said compounds.

3-tert-Butyl-4-chlorophenol of this invention can be prepared by chlorinating 3-tert-butylphenol with sulfuryl chloride, chlorine or various kinds of chlorimating agents. In addition, this compound can be prepared by chlorinating boric ester of 3-tert-burylphenol, followed by hydrolysis of said ester.

On the other hand, 4-bromo-3-tert-butylphenol of this invention can be prepared by brominating boric acid ester of 3-tert-butylphenol obtained through a reaction of 3-tert-butylphenol with boric acid, followed by hydrolysis of said ester.

In said reaction of 3-tert-butylphenol with sulfuryl chloride to prepare 3-tert-butyl-4-chlorophenol of this invention, a reasonable catalyst can be used that is exemplified by metal halides such as ferric chloride, aluminum chloride, zinc chloride, cuprous chloride, cupric chloride, cobalt chloride, nickel chloride and the like; metal complex compounds such as iron (III) acetylacetonate and the like.

In order for the reaction to proceed smoothly, a reasonable solvent can be used that is preferably exemplified by halogenated hydrocarbons such as dichloromethane, chloroform, carbon tetrachloride, dichloroethane and the like. The reaction temperature thereof is preferably 0° C. to about 120° C., more preferably 30° C. to about 80° C.

The reaction period thereof is preferably several ten minutes to about 48 hours.

On the other hand, 4-bromo-3-tert-butylphenol can be prepared by brominating boric acid ester obtained through a reaction of 3-tert-butylphenol with boric acid, followed by hydrolysis of said ester.

In said reaction to give the boric acid ester of 3-tert-butylphenol, 3-tert-butylphenol and boric acid are added into a solvent, which forms an azeotropic mixture with water andd is immiscible with water, such as benzene, toluene, xylene and the like and are subjected to dehydration treatment by refluxing with heating to afford the boric acid ester as a single substance of orthoborate, cyclic borate and the like, or a mixture thereof in various kind of ratio.

In order to facilitate the reaction of brominating boric acid ester of 3-tert-butylphenol with bromine smoothly, a reasonable solvent can be employed. As said solvent, halogenated hydrocarbons such as dichloromethane, chloroform, carbon tetrachloride, dichloroethane and the like are suitable. The reaction temperature is preferably −10° C. to about 80° C. and the reaction period is preferably several minutes to about 24 hours.

After completion of the bromination reaction, suitable amount of water is added into the resultant mixture to afford a reaction product.

EXAMPLES

Next, this invention is explained by the following examples, but this invention is not restricted to only these examples.

EXAMPLE 1

Into 30 ml of carbon tetrachloride were dissolved 9 g of 3-tert-butylphenol and the mixture was heated up to 70° C. With stirring at this temperature, 10.5 g of sulfuryl chloride were added dropwise to the mixture. After completion of this dropwise addition, the reaction mixture was subjected to stirring over a period of 48 hours at 70° C. After cooling the reaction mixture down to room temperature, the reaction mixture was poured into cold water and the resultant product was extracted with carbon tetrachloride. After drying over anhydrous calcium chloride, carbon tetrachloride of the extraction solution was distilled off under reduced pressure, and the residue was purified through a column chromatography (employing silica gel as carrier and benzene as developing solvent) to give 1.3 g of 3-tert-butyl-4-chlorophenol, having the following properties.

$n_D^{25}$ 1.5424.

Characteristic absorptions of IR spectrum (NaCl, cm$^{-1}$) 3340, 2980, 1605, 1580, 1470, 1370, 1285, 1225.

NMR spectrum (CDCl$_3$, δ=ppm) 1.35 (9H, s) 5.41 (1H, s) 6.51 (1H, dd) 6.85 (1H, d) 7.11 (1H, d).

| Elemental analysis (%) | | |
|---|---|---|
| Found | C: 65.12 | H: 7.27 |
| Calculated | C: 65.04 | H: 7.09 |

EXAMPLE 2

Into 50 ml of dichloroethane were dissolved 30 g of 3-tert-butylphenol, and further 0.1 g of ferric chloride was added thereto. The reaction mixture was heated up to 60° C. and, with stirring at this temperature, 35.1 g of sulfuryl chloride were added dropwise thereto. After completion of this dropwise addition, the reaction mixture was subjected to stirring over a period of 8 hours at 60° C. After cooling the reaction mixture down to room temperature, it was poured into cold water and the resultant product was extracted with dichloroethane.

After drying over anhydrous calcium chloride, dichloroethane of the extracted solution was distilled off under reduced pressure. The residue was purified through reduced distillation to give 13.6 g of 3-tert-butyl-4-chlorophenol having boiling point of 101°–102° C./0.8 mmHg.

EXAMPLE 3

To 50 ml of toluene were added 8.25 g of 3-tert-butylphenol and 1.5 g of boric acid, and the mixture was subjected to dehydration treatment until water was no longer formed by refluxing with heating and stirring in use of a water-determining receiver. Then, toluene of the reaction mixture was distilled off under reduced pressure to afford boric acid ester of 3-tert-butylphenol as residue thereof.

Following this, to this boric acid ester were added 50 ml of chloroform as a solvent, and a solution obtained by dissolving 9 g of bromine into 20 ml of chloroform was added dropwise thereto. After completion of this dropwise addition, the reaction mixture was subjected to stirring over a period of 16 hours at room temperature. After adding 100 ml of water, the reaction mixture was further subjected to stirring over a period of 4 hours at room temperature. Chloroform layer was separated, washed with water and a saturated aqueous solution of sodium chloride in this order, and dried over anhydrous calcium chloride, from which the solvent was afterwards distilled off under reduced pressure. The residue was purified through a column chromatography (employing silica gel as carrier and benzene as developing solvent) to give 2.39 g of 4-bromo-3-tert-butylphenol, of which properties are as follows:

$n_D^{25}$ 1.5601

Characteristic absorptions of IR spectrum (NaCl, cm$^{-}$) 3340, 2960, 1595, 1575, 1470, 1365, 1285, 1225.

NMR spectrum (CDCl$_3$, $\delta$=ppm) 1.40 (9H, s) 5.51 (1H, s) 6.45 (1H, dd) 6.88 (1H, d) 7.33 (1H, d).

| Elemental analysis (%) | | |
|---|---|---|
| Found: | C: 52.53 | H: 5.85 |
| Calculated | C: 52.42 | H: 5.71 |

EXAMPLE 4

To 100 ml of toluene were added 15 g of 3-tert-butylphenol and 4.7 g of boric acid, which afterwards afforded boric acid ester of 3-tert-butylphenol through the same reaction procedure as in Example 3.

To this boric acid ester were added 100 ml of carbon tetrachloride, and a solution obtained by dissolving 17 g of bromine into 50 ml of carbon tetrachloride was added dropwise thereto with stirring at room temperature. After completion of this dropwise addition, the reaction mixture was subjected to stirring for one hour at 60° C. Then, the same reaction procedure as in Example 3 was conducted to give 5.3 g of 4-bromo-3-tert-butylphenol.

Next, reference examples and application examples of specified carbamate derivatives which are obtained by employing 3-tert-butyl-4-halophenols of this invention as the starting compounds are shown as follows.

The above specified carbamate derivatives can be represented by the formula (I).

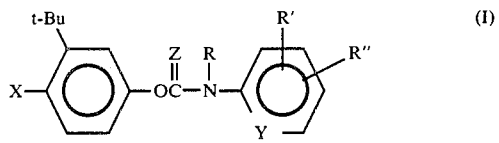

(I)

wherein X denotes halogen atom, Y denotes methine group or nitrogen atom, Z denotes oxygen atom or sulfur atom, R denotes lower alkyl group, and R', R" denote hydrogen atom, halogen atom, lower alkyl group, or lower alkoxy group respectively.

REFERENCE EXAMPLE 1

To 30 ml of acetone were added 2.04 g of N-(3-chlorophenyl)-N-methylcarbamoyl chloride, 1.84 g of 3-tert-butyl-4-chlorophenol and 1.6 g of anhydrous potassium carbonate, and the mixture was refluxed with heating for 48 hours. The reaction mixture was cooled down to room temperature and thereafter was poured into cold water. The product was extracted with benzene. The benzene solution was washed with water and a saturated aqueous solution of sodium chloride in this order, and was dried over anhydrous magnesium sulfate. Thereafter, benzene was distilled off. The residue was purified through a column chromatography (employing silica gel as carrier and benzen as developing solvent), and further recrystallized from hexane to give 3.2 g of 3-tert-butyl-4-chlorophenyl N-(3-chlorophenyl)-N-methylcarbamate, having melting point of 65°–67° C.

REFERENCE EXAMPLE 2

Into 50 ml of chloroform were dissolved 9.2 g of 3-tert-butyl-4-chlorophenol and 6.3 g of thiophosgene, and 60 ml of 1N-sodium hydroxide solution were added dropwise thereto with stirring at room temperature. After completion of this dropwise addition, the mixture was subjected to stirring over a period of 3 hours. From the reaction mixture was separated chloroform layer, which was thereafter dried over anhydrous calcium chloride. Then, chloroform was distilled off and the residue was distilled under reduced pressure to give 9.5 g of O-3-tert-butyl-4-chlorophenyl chlorothioformate having boiling point of 103°–106° C./0.5 mmHg, of which properties are as follows.

$n_D^{25}$ 1.5663

| Elemental analysis (%) | | |
|---|---|---|
| Found | C: 50.25 | H: 4.45 |
| Calculated | C: 50.20 | H: 4.59 |

To 20 ml of acetone were added 1.07 g of N-methylaniline and 1.38 g of anhydrous potassium carbonate, and a solution obtained by dissolving 2.63 g of O-3-tert-butyl-4-chlorophenyl chlorothioformate into 20 ml of acetone was added thereto with stirring at room temperature. After stirring for 30 minutes as it is, the mixture was subjected to refluxing with heating for 2 hours. The reaction mixture was cooled down to room temperature and then poured into cold water. The product was extracted with benzene. The benzene solution was washed with water and a saturated aqueous solution of sodium chloride in this order, and dried over anhydrous magnesium sulfate. Thereafter, benzene was distilled off. The residue was purified through a column chromatography (employing silica gel as carrier, and benzene/hexane=1/1 (V/V) as developing solvent) and further recrystallized form ethanol to give 2.64 g of O-3-tert-butyl-4-chlorophenyl N-methyl-N-phenylthiocarbamate, having melting point of 65°–67° C.

REFERENCE EXAMPLE 3

Into 50 ml of benzene were dissolved 9.2 g of 3-tert-butyl-4-chlorophenol and 5.5 g of trichloromethyl chloroformate, and a solution obtained by dissolving 5.8 g of triethylamine into 20 ml of benzene was added dropwise thereto with stirring and cooling by ice. After completion of this dropwise addition, the mixture was subjected to stirring for 12 hours at room temperature. To the reaction mixture were added 70 ml of hexane, and precipitated crystal was separated by filtration. The filtrate was washed with water and a saturated aqueous solution of sodium chloride in this order, and was dried over anhydrous calcium chloride. Thereafter, solvent was distilled off. The residue was distilled under reduced pressure to give 9.32 g of 3-tert-butyl-4-chlorophenyl chloroformate having boiling point of 105°–108° C./1 mmHg, of which properties are as follows.

$n_D^{25}$ 1.5232

| Elemental anylysis (%) | | |
|---|---|---|
| Found | C: 53.11 | H: 4.91 |
| Calculated | C: 53.46 | H: 4.89 |

To 20 ml of acetone were added 1.25 g of 4-fluoro-N-methylaniline and 1.38 g of anhydrous potassium carbonate, and a solution obtained by dissolving 2.5 g of 3-tert-butyl-4-chlorophenyl chloroformate into 20 ml of acetone was added thereto with stirring at room temperature. After stirring for 30 minutes as it is, the mixture was refluxed with heating for 2 hours. After cooled down to room temperature, the reaction mixture was poured into cold water and the resultant product was extracted with benzene. The benzene solution was washed with water and a saturated aqueous solution of sodium chloride in this order, dried over anhydrous magnesium sulfate, and thereafter benzene was distilled off under reduced pressure. The residue was purified through a column chromatography (employing silica gel as carrier and benzene as developing solvent) and further recrystallized from ethanol to give 2.7 g of 3-tert-butyl-4-chlorophenyl N-(4-fluorophenyl)-N-methylcarbamate having melting point of 92°–94° C.

REFERENCE EXAMPLE 4

The following specified carbamate derivatives (1)–(20) represented by the aforesaid formula (I) were prepared according to the same reaction procedure as in the above reference examples.

(1) 3-tert-Butyl-4-chlorophenyl N-methyl-N-phenylcarbamate.
Melting point 59.5°–60.5° C.

| Elemental anylysis (%) | | | |
|---|---|---|---|
| Found | C: 68.33 | H: 6.45 | N: 4.67 |
| Calculated | C: 68.02 | H: 6.34 | N: 4.40 |

(2) 3-tert-Butyl-4-chlorophenyl N-(3-chlorophenyl)-N-methylcarbamate.
Melting point 65°–67° C.

| Elemental analysis (%) | | | |
|---|---|---|---|
| Found | C: 61.74 | H: 5.45 | N: 3.96 |
| Calculated | C: 61.37 | H: 5.43 | N: 3.97 |

(3) 3-tert-Butyl-4-chlorophenyl N-methyl-N-(3-methylphenyl)carbamate.
Melting point 49.5°–51.5° C.

| Elemental analysis (%) | | | |
|---|---|---|---|
| Found | C: 69.04 | H: 6.83 | N: 4.47 |
| Calculated | C: 68.77 | H: 6.68 | N: 4.22 |

(4) 3-tert-Butyl-4-chlorophenyl N-(3-methoxyphenyl)-N-methylcarbamate.
Melting point 35°–38° C.

| Elemental analysis (%) | | | |
|---|---|---|---|
| Found: | C: 65.20 | H: 6.29 | N: 4.33 |
| Calculated | C: 65.60 | H: 6.37 | N: 4.02 |

(5) 3-tert-Butyl-4-chlorophenyl N-(6-methoxy-2-pyridyl)-N-methylcarbamate.
Melting point 54°–56° C.

| Elemental analysis (%) | | | |
|---|---|---|---|
| Found | C: 62.04 | H: 5.95 | N: 7.74 |
| Calculated | C: 61.97 | H: 6.06 | N: 8.03 |

(6) O-3-tert-Butyl-4-chlorophenyl N-methyl-N-phenylthiocarbamate.
Melting point 65°–67° C.

| Elemental analysis (%) | | | |
|---|---|---|---|
| Found | C: 64.48 | H: 5.94 | N: 4.31 |
| Calculated | C: 64.75 | H: 6.03 | N: 4.19 |

(7) O-3-tert-Butyl-4-chlorophenyl N-methyl-N-(3-methylphenyl)thiocarbamate.
Melting point 85.5°–86.5° C.

| Elemental analysis (%) | | | |
|---|---|---|---|
| Found | C: 65.80 | H: 6.32 | N: 4.12 |
| Calculated | C: 65.59 | H: 6.37 | N: 4.02 |

(8) O-3-tert-Butyl-4-chlorophenyl N-(3-methoxphenyl)-N-methylthiocarbamate.
Melting point 110°–111.5° C.

| Elemental analysis (%) | | | |
|---|---|---|---|
| Found | C: 62.67 | H: 5.91 | N: 4.13 |
| Calculated | C: 62.71 | H: 6.09 | N: 3.84 |

(9) O-3-tert-Butyl-4-chlorophenyl N-(6-methoxy-2-pyridyl)-N-methyl thiocarbamate.
Melting point 123°–124° C.

| Elemental analysis (%) | | | |
|---|---|---|---|
| Found | C: 59.61 | H: 5.72 | N: 7.54 |
| Calculated | C: 59.25 | H: 5.80 | N; 7.67 |

(10) 3-tert-Butyl-4-chlorophenyl N-methyl-N-(2-methylphenyl)carbamate.
Oil.

| Elemental analysis (%) | | | |
|---|---|---|---|
| Found | C: 68.71 | H: 6.70 | N: 4.56 |
| Calculated | C: 68.77 | H: 6.68 | N: 4.22 |

(11) 3-tert-Butyl-4-chlorophenyl N-methyl-N-(4-methylphenyl)carbamate.
Oil.

| Elemental analysis (%) | | | |
|---|---|---|---|
| Found | C: 68.42 | H: 6.62 | N: 3.84 |

| Elemental analysis (%) | | | |
|---|---|---|---|
| Calculated | C: 68.77 | H: 6.68 | N: 4.22 |

(12) 3-tert-Butyl-4-chlorophenyl N-(2-fluorophenyl)-N-methylcarbamate.
Melting point 70°–71° C.

| Elemental analysis (%) | | | |
|---|---|---|---|
| Found | C: 64.32 | H: 5.71 | N: 4.33 |
| Calculated | C: 64.38 | H: 5.70 | N: 4.17 |

(13) 3-tert-Butyl-4-chlorophenyl N-(3-fluorophenyl)-N-methylcarbamate.
Melting point 61°–62.5° C.

| Elemental analysis (%) | | | |
|---|---|---|---|
| Found | C: 64.21 | H: 5.63 | N: 3.92 |
| Calculated | C: 64.38 | H: 5.70 | N: 4.17 |

(14) 3-tert-Butyl-4-chlorophenyl N-(4-fluorophenyl)-N-methylcarbamate.
Melting point 92°–94° C.

| Elemental analysis (%) | | | |
|---|---|---|---|
| Found | C: 64.31 | H: 5.56 | N: 3.79 |
| Calculated | C: 64.38 | H: 5.70 | N: 4.17 |

(15) 3-tert-Butyl-4-chlorophenyl N-(3-bromophenyl)-N-methylcarbamate.
Melting point 80°–82° C.

| Elemental analysis (%) | | | |
|---|---|---|---|
| Found | C: 54.12 | H: 4.96 | N: 3.42 |
| Calculated | C: 54.49 | H: 4.82 | N: 3.53 |

(16) 3-tert-Butyl-4-chlorophenyl N-methyl-N-(3,4-dimethylphenyl)carbamate.
Oil.

| Elemental analysis (%) | | | |
|---|---|---|---|
| Found | C: 69.53 | H: 6.85 | N: 4.14 |
| Calculated | C: 69.45 | H: 6.99 | N: 4.04 |

(17) 3-tert-Butyl-4-chlorophenyl N-methyl-N-(3,5-dimethylphenyl)carbamate.
Melting point 69°–71° C.

| Elemental analysis (%) | | | |
|---|---|---|---|
| Found | C: 69.09 | H: 6.87 | N: 4.01 |
| Calculated | C: 69.45 | H: 6.99 | N: 4.04 |

(18) 3-tert-Butyl-4-chlorophenyl N-(3-chloro-4-methylphenyl)-N-methylcarbamate.
Melting point 116°–117° C.

| Elemental analysis (%) | | | |
|---|---|---|---|
| Found | C: 62.54 | H: 5.86 | N: 3.65 |

| Elemental analysis (%) | | | |
|---|---|---|---|
| Calculated | C: 62.30 | H: 5.77 | N: 3.82 |

(19) 3-tert-Butyl-4-chlorophenyl N-ethyl-N-phenylcarbamate.
Melting point 85°–88° C.

| Elemental analysis (%) | | | |
|---|---|---|---|
| Found | C: 68.60 | H: 6.82 | N: 4.42 |
| Calculated | C: 68.77 | H: 6.68 | N: 4.22 |

(20) 3-tert-Butyl-4-chlorophenyl N-ethyl-N-(3-methylphenyl)carbamate.
Melting point 69°–71° C.

| Elemental analysis (%) | | | |
|---|---|---|---|
| Found | C: 69.21 | H: 6.97 | N: 4.05 |
| Calculated | C: 69.45 | H: 6.99 | N: 4.04 |

REFERENCE EXAMPLE 5

To 30 ml of acetone were added 1.7 g of N-methyl-N-phenyl-carbomoylchloride, 2.29 g of 4-bromo-3-tert-butylphenol and 1.4 g of anhydrous potassium carbonate, which was thereafter refluxed with heating for 48 hours. After cooled down to room temperature, the reaction mixture was poured into cold water and the resultant product was extracted with benzene. The benzene solution was washed with water and a saturated aqueous solution of sodium chloride in this order, dried over anhydrous magnesium sulfate, and then benzene was distilled off therefrom. The residue was purified through a column chromatography (employing silica gel as carrier and benzene as developing solvent) to give 3.04 g of 4-bromo-3-tert-butylphenyl N-methyl-N-phenylcarbamate. Oil.

REFERENCE EXAMPLE 6

To 50 ml of chloroform were dissolved 11.5 g of 4-bromo-3-tert-butylphenol and 6.5 g of thiophosgene, and 60 ml of 1-N sodium hydroxide aqueous solution were added dropwise thereto with stirring at room temperature. After completion of this dropwise addition, the mixture was subjected to stirring over a period of 3 hours at room temperature. From the reaction mixture was separated chloroform layer, which was thereafter dried over anhydrous calcium chloride and then chloroform was distilled off therefrom. The residue was purified through a column chromatography (employing silica gel as carrier and hexane as developing solvent) to give 10.3 g of O-4-bromo-3-tert-butylphenyl chlorothioformate.
$n_D^{25}$ 1.5823.

| Elemental analysis (%) | | |
|---|---|---|
| Found | C: 42.59 | H: 3.89 |
| Calculated | C: 42.94 | H: 3.93 |

To 20 ml of acetone were added 1.37 g of 3-methoxy-N-methylaniline and 1.38 g of anhydrous potassium carbonate, and a solution obtained by dissolving 3.08 g of O-4-bromo-3-tert-butylphenyl chlorothioformate into 20 ml of acetone was added thereto with stirring at room temperature. After stirring for 30 minutes as it is, the mixture was refluxed with heating for 2 hours. After cooled down to room temperature, the reaction mixture was poured into cold water and the resultant product was extracted with benzene. The benzene solution was washed with water and a saturated aqueous solution of sodium chloride in this order, dried over anhydrous magnesium sulfate, and then benzene was distilled off therefrom. The residue was purified through a column chromatography (employing silica gel as carrier and benzene/hexane=1/1 (V/V) as developing solvent) and further recrystallized from benzene-hexane to give 2.61 g of O-4-bromo-3-tert-butylphenyl N-(3-methoxyphlnyl)-N-methylthiocarbamate.

Melting point 115°-116° C.

REFERENCE EXAMPLE 7

The following specified carbamate derivatives (21)-(29) represented by the aforesaid formula (I) were prepared according to the same reaction procedure as in the reference Example 5 and 6.

(21) O-4-Bromo-3-tert-butylphenyl N-(6-methoxy-2-pyridyl)-N-methylthiocarbamate.

Melting point 117°-119° C.

| Elemental analysis (%) | | | |
|---|---|---|---|
| Found | C: 52.83 | H: 5.07 | N: 6.70 |
| Calculated | C: 52.81 | H: 5.17 | N: 6.84 |

(22) O-4-Bromo-3-tert-butylphenyl N-methyl-N-(3-methylphenyl)thiocarbamate.

Melting point 91°-93° C.

| Elemental analysis (%) | | | |
|---|---|---|---|
| Found | C: 58.18 | H: 5.78 | N: 3.94 |
| Calculated | C: 58.16 | H: 5.65 | N: 3.56 |

(23) 4-Bromo-3-tert-butylphenyl N-methyl-N-phenylcarbamate.

Oil.

| Elementary analysis (%) | | | |
|---|---|---|---|
| Found | C: 59.28 | H: 5.51 | N: 3.48 |
| Calculated | C: 59.67 | H: 5.56 | N: 3.86 |

(24) 4-Bromo-3-tert-butylphenyl N-(3-chlorophenyl)-N-methylcarbamate.

Oil.

| Elemental analysis (%) | | | |
|---|---|---|---|
| Found | C: 54.11 | H: 4.93 | N: 3.80 |
| Calculated | C: 54.49 | H: 4.82 | N: 3.53 |

(25) 4-Bromo-3-tert-butylphenyl N-methyl-N-(3-methylphenyl)carbamate.

Oil.

| Elemental analysis (%) | | | |
|---|---|---|---|
| Found | C: 60.71 | H: 6.01 | N: 4.00 |
| Calculated | C: 60.64 | H: 5.89 | N: 3.72 |

(26) 4-Bromo-3-tert-butylphenyl N-(3-methoxyphenyl)-N-methylcarbamate.

Oil.

| Elemental analysis (%) | | | |
|---|---|---|---|
| Found | C: 57.96 | H: 5.56 | N: 3.68 |
| Calculated | C: 58.17 | H: 5.65 | N: 3.57 |

(27) 4-Bromo-3-tert-butylphenyl N-(6-methoxy-2-pyridyl)-N-methylcarbamate.

Melting point 78°-79° C.

| Elemental analysis (%) | | | |
|---|---|---|---|
| Found | C: 55.06 | H: 5.47 | N: 7.16 |
| Calculated | C: 54.97 | H: 5.38 | N: 7.12 |

(28) O-4-Bromo-3-tert-butylphenyl N-methyl-N-phenylthiocarbamate.

Melting point 60°-62° C.

| Elemental analysis (%) | | | |
|---|---|---|---|
| Found | C: 57.27 | H: 5.36 | N: 3.78 |
| Calculated | C: 57.14 | H: 5.32 | N: 3.70 |

(29) O-4-Bromo-3-tert-butylphenyl N-(3-methoxyphenyl)-N-methylthiocarbamate.

Melting point 115°-116° C.

| Elemental analysis (%) | | | |
|---|---|---|---|
| Found | C: 56.09 | H: 5.57 | N: 3.35 |
| Calculated | C: 55.88 | H: 5.43 | N: 3.43 |

The specified carbamate derivatives which can be prepared from 3-tert-butyl-4-halophenols of this invention are not restricted to the above these reference examples 1-7.

APPLICATION EXAMPLE

A water dispersible powder containing these carbamate derivatives in 10% concentration as an effective ingredient was prepared. A submerged treatment test before germination of weeds was conducted immediately after transplanting young seedling of rice plant in condition of water paddy field, employing porcelain pots having a diameter of 9 cm, and herbicidal activities against various kind of weeds and influences against the rice plant were examined. As the result, even a dosage of 1000 g/10 acres was not recognized to give substantial phytotoxicity in case of employing any effective ingredient. Moreover, the weeds of paddy field such as barnyard grass (Echinochloa Crus-galli P. Beauv. var. oryjicola Ohwi.), umbrella plant (Cyperus difformis L.), Monochoria (Monochoria vaginalis Presl.), toothcup (Rotala indica Koehne. var. uliginosa Miq.) and the like could be eliminated in amount of effective ingredient of about 15-500 g/10 acres which showed however some displacement depending on the kind of effective ingredient.

What is claimed is:

1. A method for preparing 3-tert-butyl-4-chlorophenol comprising the step of reacting 3-tert-butylphenol with 1-1.2 equivalents of sulfuryl chloride under the absence or presence of metal halides as catalysts in the absence or presence of halogenated hydrocarbons at a temperature in the range 0° C.–120° C.

2. The method of claim 1 wherein said metal halide is selected from the group consisting of ferric chloride, aluminum chloride, zinc chloride, cuprous chloride, cupric chloride, cobalt chloride and nickel chloride.

3. The method of claim 1 wherein said halogenated hydrocarbon is selected from the group consisting of dichloromethane, chloroform, carbon tetrachloride, and dichloroethane.

* * * * *